United States Patent [19]

Diesen

[11] Patent Number: 5,276,257
[45] Date of Patent: Jan. 4, 1994

[54] PROCESS FOR CONVERTING BUTADIENE TO STYRENE OR ETHYLBENZENE OR BOTH USING CATALYSTS CONTAINING MOLYBDENUM

[75] Inventor: Ronald W. Diesen, Midland, Mich.

[73] Assignee: The Dow Chemical Company, Midland, Mich.

[21] Appl. No.: 911,228

[22] Filed: Jul. 9, 1992

[51] Int. Cl.$^5$ .................... C07C 2/00; C07C 6/00
[52] U.S. Cl. .................... 585/417; 585/407; 585/415; 585/420; 585/421
[58] Field of Search ............... 585/407, 415, 417, 420, 585/421

[56] References Cited

U.S. PATENT DOCUMENTS

| | | |
|---|---|---|
| 2,316,271 | 4/1943 | Mattox . |
| 2,376,309 | 5/1945 | Dixon . |
| 2,376,985 | 5/1945 | Voorhees . |
| 2,387,836 | 10/1945 | Dixon . |
| 2,392,960 | 1/1946 | Watson . |
| 2,438,041 | 3/1948 | Dutcher . |
| 2,941,016 | 6/1960 | Schmetterling et al. ............ 585/420 |
| 3,054,837 | 9/1962 | Janoski . |
| 3,207,801 | 9/1965 | Frilette et al. . |
| 3,546,313 | 12/1970 | Banks . |
| 3,769,238 | 10/1973 | Tauster et al. . |
| 3,830,866 | 8/1974 | D'Alessandro et al. . |
| 3,903,185 | 9/1975 | Vogel et al. . |
| 4,029,715 | 6/1977 | Rieve et al. . |
| 4,036,901 | 7/1977 | Kawakami et al. . |
| 4,291,180 | 9/1981 | Kiikka .................. 585/320 |
| 4,629,719 | 12/1986 | Kukes et al. ........... 502/242 |
| 4,973,791 | 11/1990 | Vrieland et al. ........ 585/624 |

OTHER PUBLICATIONS

Csicsery, "Dehydrocydodimerization", Ind. Eng. Chem. Process Des. Pev. vol. 18, No. 2, pp. 191–197 (1979).

Primary Examiner—Patrick P. Garvin
Assistant Examiner—E. D. Irzinski
Attorney, Agent, or Firm—Robert M. O'Keefe

[57] ABSTRACT

Butadiene is converted to ethylbenzene or styrene or both by contacting butadiene with a catalyst containing molybdenum.

9 Claims, No Drawings

PROCESS FOR CONVERTING BUTADIENE TO STYRENE OR ETHYLBENZENE OR BOTH USING CATALYSTS CONTAINING MOLYBDENUM

BACKGROUND OF THE INVENTION

The present invention relates to methods for converting unsaturated hydrocarbons to aromatic compounds.

Ethylbenzene is an important commercial solvent and a precursor to styrene. Styrene is a major commercial chemical which finds its principal use in the manufacture of polymers such as polystyrene. Typically, styrene is formed by the dehydrogenation of ethylbenzene. Both ethylbenzene and styrene may be produced by catalytic dehydrocyclization of 4-vinylcyclohexene ("VCH") by use of various known catalysts. Two-step processes for producing styrene and ethylbenzene are also known wherein butadiene is dimerized to form VCH and the VCH is then catalytically aromatized.

However, the prior art lacks methods of producing styrene and ethylbenzene directly from butadiene. Methods for the aromatization of VCH, moreover, have been plagued with poor yields and large amounts of by-products such as xylene with are extremely difficult to separate from the styrene and ethylbenzene.

What is needed are new, more selective and effective processes for the production of aromatics such as ethylbenzene and styrene which alleviate problems in the prior art. What is also needed is a process to produce aromatics directly from butadiene thereby offering a new method of producing the aromatics in one step.

SUMMARY OF INVENTION

This invention, in one respect, is a process for the production of aromatic compounds from butadiene which comprises contacting a feedstream comprising butadiene with a catalyst under conditions effective to convert a least a portion of the butadiene to ethylbenzene or styrene or both, wherein the catalyst is an oxide of molybdenum and a Group IA alkali metal promoter on a support selected from the group consisting of silica, alumina, or a magnesium-alumina composite, or an oxide of molybdenum, an oxide of magnesium, and a Group IA alkali metal promoter, and wherein the oxide of molybdenum in the catalyst has an oxidation state less than or equal to +6 and greater than +4.

It has been found that butadiene can be converted to ethylbenzene or styrene or both by catalytic aromatization in the presence of certain molybdenum containing catalysts.

DETAILED DESCRIPTION OF ILLUSTRATIVE EMBODIMENT

A first catalyst useful in the present invention is described in U.S. Pat. No. 4,973,791, incorporated herein by reference. Generally, the catalyst may be described as consisting essentially of molybdenum oxide and potassium on a magnesium oxide support. This first catalyst is described in U.S. Pat. No. 4,973,791 as a solid heterogeneous oxide, at least a portion of the oxygen of which is labile. By this is meant that a free form of oxygen is capable of oxidizing the aliphatic hydrocarbon. After the labile oxygen is removed through the oxidation reaction described in U.S. Pat. No. 4,973,791, the catalyst is further described as being spent and may build up a carbonaceous residue on its surface over time. U.S. Pat. No. 4,973,791 teaches that the catalyst is useful for oxidizing aliphatic hydrocarbons to unsaturated aliphatic hydrocarbons. The molybdenum of the fresh catalyst has an oxidation state of about +6. However, it has now been found that catalyst wherein the molybdenum has an oxidation state less than or equal to +6 and greater than +4 can be employed to catalyze the formation of styrene as the major product from VCH.

A second suitable catalyst is a a molybdate catalyst composition comprising a support component and a catalyst component. This catalyst is disclosed in pending U.S. patent application Ser. No. 07/505,751, filed Apr. 6, 1990, the teachings of which are incorporated by reference. The support contains magnesium oxide and at least one aluminum oxide selected from the group consisting of alumina ($Al_2O_3$) and magnesium aluminate spinel ($MgAl_2O_3$). The support has a MgO/$Al_2O_3$ weight ratio in the range from about 0.30 to about 4.0 and a surface area of at least about 25 $m^2/g$. The catalyst component consists essentially of an oxide of molybdenum, an oxide of magnesium, and a promoting amount of an alkali metal promoter. Optionally, the catalyst may contain an oxide of vanadium. The molybdenum in the second molybdate catalyst composition has an oxidation state less than or equal to +6 and greater than +4.

The aluminum oxide primarily imparts hardness and attrition resistance to the catalyst particles, so that they might be more suitable for use in fluid bed or transport reactors. Any source of aluminum oxide is acceptable, including $\alpha$-, $\beta$-, and $\gamma$-aluminas, hydrated alumina, such as boehmite alumina, aqueous colloidal alumina, stoichiometric $Al(OH)_3$, and aluminum alkoxides, as noted hereinbelow. Magnesium aluminate and magnesium aluminate hydroxides are also suitable sources of aluminum oxide. The magnesium oxide functions in a dual role: first, as a support for the catalyst components, and secondly, as a basic catalyst component which neutralizes the acidity of the alumina and other residual acid sites. It is highly desirable for the catalyst to be basic, because basicity enhances the desorption of products. Any source of magnesium oxide is acceptable; however, MgO and $Mg(OH)_2$ are preferred. Any source of molybdenum oxide is acceptable, including for example, $MoO_3$, $(NH_4)_6Mo_7O_{24}·4H_2O$, and $(NH_4)_2MoO_4$. The molybdenum oxide can also be obtained from a precursor molybdenum compound, such as molybdenum carbonyls, e.g., $Mo(CO)_6$. Preferably, the source of molybdenum oxide is ammonium heptamolybdate represented by the formula $(NH_4)_6MO_7O_{24}·4H_2O$. The alkali metal promoter functions to increase the basicity of the catalyst, thereby increasing the selectivity of higher unsaturates in the process of this invention. The alkali metal promoter is a Group IA metal compound. Small amounts of other elements may be present in the catalyst, provided that these elements do not materially change the performance of the catalyst.

It is noted that the support component may contain a spinel ($MgAl_2O_4$) phase. The weight percentage of spinel in the support component can range from 0 percent to about 100 percent.

Typically, the preparation of the catalyst begins with the combination of the magnesium oxide and aluminum oxide components to form a support for the other catalytic components. Any method of combination of these components is suitable; however, there are three preferred methods. The first method comprises impregnating a preformed spinel ($MgAl_2O_4$) with a solution containing a soluble magnesium salt, such as magnesium nitrate, magnesium chloride, magnesium sulfate, magnesium acetate or the like, provided that the salt can be converted to magnesium oxide on calcination; and thereafter calcining the impregnated spinel. The weight ratio of magnesia to magnesium aluminate can be conveniently expressed as a weight ratio of magnesia to alumina. This ratio is critical to the performance of the catalyst composition and is discussed separately hereinbelow. The temperature of calcination typically ranges from about 400° C. to about 1200° C., preferably, from about 450° C. to about 900° C., more preferably, from about 500° C. to about 700° C. The calcination is conducted for a time sufficient to form a fused composite which can function as a support for the catalytic components, but at least about 0.5 hour.

The second method involves impregnating a preformed alumina with a solution of a soluble magnesium salt, such as those identified hereinabove. Pre-formed aluminas are defined herein as anhydrous or hydrated solid aluminas, of which $\alpha$-, $\beta$-, and $\gamma$-aluminas and boehmite alumina are typical examples. The weight ratio of magnesia to alumina, $MgO/Al_2O_3$, is a critical parameter which is discussed in detail hereinbelow. The temperature of calcination typically ranges from about 400° C. to about 1200° C., preferably, from about 450° C. to about 900° C., more preferably, from about 500° C. to about 700° C. The calcination is conducted for a time sufficient to form a fused and hardened composite which can function as a support for the catalytic components. Typically, the calcination is conducted for at least about 0.5 hour. During calcination a portion of the alumina and magnesia may chemically combine to form a spinel phase, $MgAl_2O_4$, which is intimately mixed between the domains of magnesia and alumina.

The third method of preparing the support comprises adding colloidal alumina to magnesium oxide and drying the resulting mixture under conditions sufficient to prepare a magnesia-alumina support. Colloidal alumina is an acidified aqueous suspension of hydrated aluminum oxide, wherein the particle surface area is so much greater than its volume that the particles are not settled out by gravity. A quantity of colloidal alumina suspension is added to the magnesia such that the final magnesia to alumina weight ratio falls within the range specified hereinafter. The pH of the colloidal alumina and magnesia mixture is about 9. The mixture is dried by any one of a variety of techniques, including aging and evaporating, spray-drying, flash drying, tunnel drying, drum drying and the like. One preferred method involves aging and evaporating the mixture over a hot plate or equivalent heating means to form a thicker gel and eventually a hard solid mass, which is crushed and sieved to the desired particle size. The temperature of the aging and evaporation process is any which is compatible with the solvent system. Since the preferred solvent system is water, the temperature is in the range from about 30° C. to about 100° C. Preferably, the temperature is in the range from about 50° C to about 90° C, more preferably, in the range from about 60° C to about 80° C. The time required for aging will depend on the quantity of gel, and is any time sufficient to obtain the solid, hard mass.

For industrial scale applications the mixture containing magnesia and colloidal alumina, prepared hereinabove, is preferably spray dried rather than aged. Any spray drying equipment which is conventionally used to produce catalyst particles suitable for use in fluidized bed reactors may be employed. For example, a Niro Atomizer S-12.5-R/N spray drying apparatus is acceptable. Such an apparatus has a means for controlling the inlet and outlet temperature. Typically, the powder particles obtained by spray drying are spheroidal in shape, range in diameter from about 10 $\mu$m to about 250 $\mu$m, and exhibit excellent flow properties.

The powder which is obtained on aging or spray drying is calcined to yield a composite support consisting essentially of magnesia and alumina, and optionally, a spinel phase of magnesium aluminate. The calcination is conducted under conditions sufficient to fuse the alumina and magnesia into a hardened mass. Generally, the calcination is conducted at a temperature in the range from about 400° C. to about 1200° C. More preferably, the calcination temperature is in the range from about 450° C. to about 900° C., most preferably in the range from about 500° C. to about 700° C. Generally, the period of calcination depends upon the amount of material to be calcined, but lasts at least for about 0.5 hour.

The support component of the second catalyst contains any weight ratio of magnesia to alumina provided that a support of sufficient hardness and basicity is obtained. Note that although the spinel phase exists as a distinct composition of $MgAl_2O_4$, a $MgO/Al_2O_3$ weight ratio is still calculable. Generally, the $MgO/Al_2O_3$ weight ratio is maintained in the range from about 0.1 to about 9.0, but ratios in the range from about 0.3 to about 4.0 are preferred. More preferred are weight ratios in the range from about 0.3 to about 2.0. Most preferred are weight ratios in the range from about 0.38 to about 0.80. Above the preferred upper ratio there may be too much magnesia and the catalyst may lack attrition resistance and toughness.

The support component of the second catalyst is further characterized by its surface area. Typically, the surface area is at least about 25 $m^2/g$. Preferably, the surface area is greater than about 35 $m^2/g$, more preferably greater than about 50 $m^2/g$. Even more preferably the surface area is from about 50 $m^2/g$ to about 250 $m^2/g$, most preferably, from about 80 $m^2/g$ to about 170 $m^2/g$. It is well-known among those skilled in the art that low surface area is generally correlated with low catalytic activity; whereas high surface area is generally correlated with high catalytic activity. The second catalyst composition of this invention exhibits both high surface area and high catalytic activity.

After the support component is prepared, the catalytic elements of molybdenum oxide, alkali metal promoter and, optionally vanadium oxide, are applied to the support. Provided that the $MgO/Al_2O_3$ weight ratio is adjusted within the suitable range identified hereinabove, there is no further need to add more magnesium oxide. Generally, the desired quantity of a molybdenum oxide or precursor compound, such as ammonium heptamolybdate or molybdenum carbonyl, is dissolved in a solvent to make a solution. Preferably, the molybdenum compound is ammonium heptamolybdate, and the solvent is water. The solution is brought into contact with the support composite, prepared hereinabove, and the resulting slurry is dried to remove solvent. If the solution is aqueous, the drying is conducted in an oven at a temperature of from about 70° C. to about 120° C. The dried slurry is thereafter calcined to form a catalytically active composition containing an aluminum oxide, magnesium oxide, and molybdenum oxide. The calcination is typically conducted at a temperature of from about 300° C. to about 900° C. for a time of from 0.5 hour to about 24 hours. Preferably, calcination is conducted at a temperature of from about 500° C to about 800° C., more preferably, from about 550° C. to about 650° C. Alternatively, the dried slurry, described hereinabove, can be employed directly with no prior calcination in the catalytic process of this invention. Since the molybdenum precursor can be converted into molybdenum oxide at or about 300° C., and since the catalyst bed is heated to a temperature higher than about 300° C, the dried composition will be converted in situ into a catalytically active aluminum oxide-magnesium oxide-molybdenum oxide mixture.

The second catalyst composition usually shows X-ray diffraction peaks characteristic of one or more of the following: magnesium oxide, magnesium molybdate, magnesium aluminate spinel, and alumina. The elemental analysis of the calcined solid reveals a composition ranging from about 3 weight percent $MoO_3$ to about 50 weight percent $MoO_3$ and from about 90 weight percent MgO to about 10 weight percent MgO with the balance being alumina. Preferably, the composition ranges from about 10 weight percent $MoO_3$ to about 30 weight percent $MoO_3$ and from about 60 weight percent MgO to about 20 weight percent MgO; more preferably, from about 12 weight percent $MoO_3$ to about 25 weight percent $MoO_3$ and from about 40 weight percent MgO to about 25 weight percent MgO.

It is required to add to the second supported catalyst described hereinbefore a promoting amount of at least one alkali metal promoter. Such a promoter is typically a compound of lithium, sodium, potassium, rubidium, cesium or francium of sufficient basicity to improve the selectivity to ethylbenzene or styrene in the process of this invention. Suitable compounds include the alkali oxides, hydroxides, and carbonates. Compounds which decompose on heating to the oxides are also suitable, such as alkali metal acetates and oxalates. Alkali metal salts may be found which are also suitable, although typically, the alkali metal halides and alkali metal silicates are not preferred due to their lower basicity. Preferably, the alkali metal promoter is an alkali metal oxide, hydroxide, carbonate, acetate, or oxalate. More preferably, the alkali metal promoter is an oxide or hydroxide of potassium or cesium. Most preferably, the alkali metal promoter is an oxide or hydroxide of potassium.

Generally, any amount of alkali metal promoter is acceptable which is sufficient to increase the selectivity and the productivity of products in the process of this invention. Typically, the amount of alkali metal promoter calculated as the alkali hydroxide is from about 0.05 weight percent to about 5 weight percent based on the total weight of the aluminum, magnesium and molybdenum oxides. Preferably, the amount of alkali metal promoter calculated as the alkali metal hydroxide is from about 0.1 weight percent to about 2 weight percent based on the total weight of the magnesium, aluminum and molybdenum oxides, more preferably from about 0.3 weight percent to about 1.5 weight percent.

The alkali metal promoter can be added to the molybdate catalyst in a variety of ways known to those in the art. For example, the promoter can be applied by the well-known impregnation technique, described for example by Charles N. Satterfield in *Heterogeneous Catalysis In Practice*, McGraw-Hill Book Company, New York, 1980, pp. 82-83, incorporated herein by reference. In this technique the molybdenum-impregnated support is immersed in a solution of the alkali metal promoter, for example, a methanolic solution of the alkali metal oxide or hydroxide. The alkali-impregnated support is then drained of excess solution, dried in an oven to remove residual solvent, and calcined at a temperature in the range from about 550° C. to about 650° C. Alternatively, the alkali metal promoter can be impregnated onto the support by the incipient wetness technique, such that the pores are filled with solution of the alkali metal oxide or hydroxide but essentially no excess solution is used. The impregnated support thus prepared is also dried in an oven to remove solvent. As a further alternative the molybdenum compound can be impregnated from the same solution as the alkali metal compound.

Optionally, the molybdate catalyst of this invention can contain an activator which functions to increase the activity of the catalyst at any given temperature. Preferably, the activator does not decrease significantly selectivity. Preferably, the activator allows the reaction to be run at a lower temperature, while achieving high selectivity and high productivity of products. Activators which are suitable for incorporation into the catalyst include the oxides of vanadium, preferably $V_2O_5$. Generally, if an activator is used, the concentration is from about 0.05 weight percent to about 10 weight percent based on the total weight of the catalyst. Preferably, the concentration of activator is from about 0.1 weight percent to about 5 weight percent, more preferably from about 0.15 weight percent to about 1.5 weight percent. The activator can be incorporated into the support and molybdenum oxide slurry prior to calcination, or can be applied to the calcined aluminum-magnesium-molybdenum oxides by the impregnation technique, described hereinbefore.

A third catalyst useful in the practice of this invention is a solid heterogeneous catalyst composition comprising a hard silica matrix and a catalytic component. This catalyst is disclosed in pending U.S. patent application Ser. No. 07/797,862, filed Nov. 26, 1991, the teachings of which are incorporated by reference. The silica matrix can be characterized as a glassy silica having a BET surface area no greater than about 20 $m^2/g$. The term "glassy" means that the silica is an amorphous and disordered phase, as determined by X-ray diffraction (XRD). Additionally, the silica can be characterized as a dense phase, meaning that it does not contain a measurable density of micropores or mesopores. A typical micropore ranges in size from about 4 angstroms to about 20 angstroms, while a typical mesopore ranges from about 20 angstroms to about 200 angstroms. The silica of this invention does, however, contain a random system of macropores characterized by large pores on the order of about 500 angstroms to about 4000 angstroms in diameter. In a visual sense, the topology of the silica is best compared to that of a sponge or irregular honeycomb. The catalytic component comprises an oxide of molybdenum and an oxide of magnesium, at least partially combined as magnesium molybdate. Preferably, the catalytic component consists essentially of an oxide of molybdenum and an oxide of magnesium. The catalytic component occurs as discrete domains of magnesium oxide containing molybdenum oxide, the domains being encapsulated in the silica matrix. The domains of the catalyst component range in size from about 0.1 micrometer to about 500 micrometers. Optionally, the catalytic component may also contain a promoting amount of alkali metal and/or an oxide of vanadium.

The silica in the third catalyst of this invention acts as an inert and hard matrix, thereby imparting a high crush strength and attrition resistance to the catalyst so that it is suitable for use in fluid bed or transport reactors. The magnesium oxide functions in a dual role: first, as a support for the active catalyst component comprising magnesium oxide and molybdenum oxide and secondly, as a base. It is believed that basicity enhances the desorption of products in the process. The molybdenum oxide contributes significantly to the catalyst's activity, especially as combined with magnesium oxide in the form of magnesium molybdate. The alkali metal promoter functions to increase the basicity of the catalyst. The alkali metal promoter is a Group IA metal compound. Small amounts of other elements may be present in the catalyst, provided that these elements do not materially change the performance of the catalyst.

As a first step in preparing the third catalyst composition of this invention, magnesium oxide is encapsulated into the aforementioned silica matrix. This preparation presents certain challenges. U.S. Pat. No. 3,678,144 teaches a method of preparing a glassy silica body having certain metal oxides bound into the silica network. The patent is silent with respect to magnesium oxide. It has now been discovered that when magnesium oxide powder is blended into an aqueous potassium silicate solution with a gellation agent according to the method of U.S. Pat. No. 3,678,144, the aqueous silicate is readily absorbed onto the surface of the magnesium oxide forming silica and magnesium silicates. The resulting hard composite material exhibits significantly reduced activity in the process of this invention. It is believed that the reduced activity is related to the presence of the surface silicates. If good phase separation exists between the magnesium oxide and silica, it is possible to maintain an active magnesium oxide surface.

The method for preparing a composite material comprising a glassy silica matrix having encapsulated therein domains of magnesium oxide comprises (a) treating a source of a metal oxide with a blocking agent, the metal oxide being selected from those which are reactive with an alkali metal silicate, (b) adding the treated source of metal oxide to an alkali metal silicate solution, (c) polymerizing the silicate to form a composite material comprising a glassy silica matrix having a BET surface area no greater than about 20 m$^2$/g and having macropores ranging in size from about 500 Å to about 4000 Å, the silica matrix having encapsulated therein domains of the source of metal oxide treated with blocking agent, and (d) calcining the composite material under conditions sufficient to remove the blocking agent and sufficient to convert the source of metal oxide into metal oxide. Optionally, the composite material may be ion-exchanged with an ammonium salt after the polymerization step (Step c) and prior to the calcination step (Step d) to reduce the concentration of alkali metal ions. Advantageously, in this preparative process the formation of deactivating surface silicates is significantly reduced. Moreover, good phase separation exists between the metal oxide and silica when compared with the process of U.S. Pat. No. 3,678,144 which does not employ blocking agent.

Any source of metal oxide is suitable for the preparation of the composite material provided that the metal oxide itself is reactive with an alkali metal silicate. The metals of Groups IIA, IIIA, IVA, and VA provide suitable reactive oxides, the group designations (IIA, IIIA, etc.) following the recommendations of the former IUPAC. Preferably, the metals are selected from the group consisting of magnesium, titanium, zirconium and niobium. More preferably, the metal is magnesium. Aside format the oxides themselves, suitable sources of such oxides include the dihydroxides, halides, nitrates, sulfates, acetates, and carbonates of the selected metal. Preferred sources include the metal oxides and hydroxides. Even more preferably, the source of metal oxide is an oxide or hydroxide of magnesium, titanium, niobium, or zirconium. Most preferably, the source of metal oxide is magnesium hydroxide or magnesium oxide. It is also beneficial for the particle size of the magnesium hydroxide to range from about 0.1 μm to about 250 μm.

The blocking agent can be any organic compound with a plurality of functional groups containing oxygen or nitrogen. Examples of blocking agents include polyols, poly(carboxylic acids), polyanhydrides, polyamines, polyamides, polyesters, polyethers, and other polyhydroxylated compounds such as cellulosics and starches. Polymers based on phenolic or phenolformaldehyde resins can also be used. Preferred block agents include Poly(vinyl alcohol) and polyacrylic and polymethacrylic acids or salts. More preferred is poly(vinyl alcohol) having a molecular weight ranging from about 1000 to about 500,000. Most preferred is poly(vinyl alcohol) having a molecular weight ranging from about 14,000 to about 115,000, available as 75-100 percent hydrolyzed acetate groups.

Typically, the blocking agent is dissolved in a suitable solvent to form a solution, and the source of metal oxide is mixed into the solution to form a second solution or gel or paste. Any solvent is acceptable provided that it is inert with respect to the blocking agent and source of metal oxide. Water is the preferred solvent, but acetone, alcohols, and other common organic solvents are also acceptable. The concentration of the blocking agent in the solvent usually ranges from about 1 weight percent to about 50 weight percent. The source of metal oxide is generally added slowly and with a high degree of agitation to the solution containing the blocking agent. The amount of blocking agent employed typically ranges from about 1 to about 20 weight percent of the weight of the source of metal oxide. The resulting solution or gel or paste is dried at a temperature in the range from about 50° C. to about 200° C. for a time sufficient to remove the solvent and form a dried solid. Thereafter, the solid is crushed and sieved to a fine powder. At this stage, a transmission electron micrograph (TEM) of the powder typically reveals that some of the particles of the source of metal oxide are coated with a layer of blocking agent, the thickness commonly ranging from about 0.1 μm to about 1 μm. Other particles, however, do not show any coating, and it is believed that the coating is thinner than the detectable limit, possibly on the order of one monolayer in thickness.

After the source of metal oxide is treated with blocking agent, the treated source is blended into an aqueous alkali metal silicate solution and the silicate is polymerized. Suitable alkali metal silicate solutions and polymerization conditions are specified in U.S. Pat. No. 3,678,144, and therefore the relevant sections of that patent are incorporated herein by reference. For example, the suitable alkali silicates include lithium silicate, sodium silicate, and potassium silicate. In order to maintain the silica in solution, the concentration of the alkali metal must be sufficient to yield a solution having a pH greater than about 10. Preferably, the alkali silicate solution is a potassium silicate solution, more preferably a commercially available potassium silicate solution containing 8.3 weight percent $K_2O$ and 20.0 weight percent $SiO_2$, the balance being water. Optionally, colloidal silica may be used in combination with the alkali silicate solution. The amount of colloidal silica which may be blended with the alkali silicate ranges form about 0 to about 30 weight percent of the total silica present.

The metal oxide source, treated with blocking agent, is blended into the alkali silicate solution very slowly and with a high degree of agitation to ensure that the solution remains smooth and fluid. The amount of alkali silicate solution, and optional colloidal silica, employed is sufficient to provide silica in the range from about 25 to about 90 weight percent based on the weight of the calcined composite material, preferably from about 35 to about 70 weight percent. The actual value will vary depending upon the end use of the composite material. In the preferred application involving a catalyst containing magnesium and molybdenum oxides, the silica concentration ranges from about 25 to about 90 weight percent based on the weight of the calcined catalyst composition.

A gellation agent is required for the polymerization of the silicate. The gellation agent functions to reduce the pH of the silicate solution by neutralizing the alkali metal ions which are present, and thereafter the silica polymerizes. Suitable gellation agents include formamide, formaldehyde, paraformaldehyde, glyoxal, ethyl acetate, and methyl acetate. Preferably, the gellation agent is formamide. Since the rate of polymerization varies with the specific gellation agent, it may be added to the alkali silicate solution either before or after the addition of the treated metal oxide source. If the gellation agent is added first, then the polymerization should not reach completion before the metal oxide source is fully blended. For example, if the gellation agent is formamide, it is usually added to the silicate solution prior to the addition of metal oxide. If the gellation agent is ethyl acetate, it should be added after the addition of metal oxide. The concentration of gellation agent is related to the concentration of alkali ions present. Typically, the concentration ranges from about 1 to about 10 weight percent based on the weight of the alkali silicate solution, preferably from about 2 to about 5 weight percent.

There are different ways of handling the viscous mixture containing the alkali silicate, the treated metal oxide source and the gellation agent. In one method, the mixture is heated in a batch in a drying ranging from about 70° C. to about 120° C. Normally the mixture sets to a hard mass within at least about 1 hour, at which time it may be broken into smaller pieces and cured. The curing process generally includes heating at a temperature in the range from about 100° C. to about 225° C. for a time ranging from about 2 hr to about 10 hr. Post cure, the dried composite is usually crushed and sieved to a powder having a particle size in the range from about 177 μm to 1190 μm (80 to 14 mesh). The particles of dried powder comprising the treated source of metal oxide encapsulated in the above-identified matrix of silica, are typically irregular in shape.

Alternatively, the viscous mixture containing the treated source of metal oxide, the gellation agent, and the alkali silicate may be suspension polymerized to yield spheroidal beads or balls having a size in the range from about 200 μm to about 1500 μm. Spheroidal particles are preferred for fluid-bed transport reactors. In this method, the mixture is added to an immiscible liquid, typically a chlorinated hydrocarbon, such as DOWTHERM E® o-dichlorobenzene commercially available from The Dow Chemical Company, at a temperature in the range from about 5° C. to about 100° C., preferably from about 10° C. to about 80° C. The addition may be effected by simply pouring the mixture into the immiscible liquid with sufficient agitation to disperse the mixture into droplets or by injecting the mixture through a droplet-forming nozzle. In order to prevent coalescence of the spheres, fumed silica may be added as a suspension agent to the chlorinated hydrocarbon. Bead size is controlled by the stirring rate of the shear mixer. Typically, a shear rate of about 300 rpm to about 725 rpm is used. This method yields hard, spheroidal beads comprising regions of the treated source of metal oxide isolated within the above-described silica matrix.

As a third alternative, the viscous mixture containing the treated source of metal oxide, the gellation agent, and the alkali silicate can be spray-dried to form spheroidal particles ranging in diameter from about 10 μm to about 250 μm. For industrial scale applications the spray-drying method is preferred. Any spray-drying equipment which is conventionally used to produce catalyst particles for fluidized bed reactors may be employed. For example, a Niro Atomizer S-12.5R/N spray drying apparatus, with a means for controlling the inlet and outlet temperatures, is acceptable.

Analysis of the composite material following polymerization of the silicate reveals good phase separation between the source of metal oxide and the silica matrix. For example, a backscattered electron image of a material produced by the polymerization of silicate in the presence of poly(vinyl alcohol)-blocked magnesium hydroxide reveals a silica/magnesium hydroxide composite. The corresponding elemental Mg map shows areas of high magnesium concentration which are identified as discrete magnesium hydroxide particles. The corresponding elemental Si map reveals that essentially no silicon resides in areas of high magnesium concentration. Additionally, potassium levels are much higher in the silicon rich areas than in areas of high magnesium concentration, as illustrated by elemental K mapping. From these data it is concluded that good separation of the magnesium hydroxide and silica phases is present. Transmission electron micrographs of the above-identified magnesium hydroxide/silica composite show predominantly crystalline magnesium hydroxide bounded by a dense, glassy silica. Again, good phase separation exists for at least about 80 percent of the composite. Up to 20 percent of the silica may appear as crystalline fines, which may contain some magnesium; however, not enough magnesium is present to indicate formation of magnesium silicate.

If desired, the composite can be leached or treated with solvents to remove the metal oxide from the silica matrix to yield a pure silica matrix. This procedure simply requires that the composite be soaked in an acid solution. In the absence of the domains of metal oxide, the silica gives the appearance of a sponge or irregular honeycomb. The BET surface area of the silica is no greater than about 20 $m^2/g$, preferably no greater than about 10 $m^2/g$, more preferably no greater than about 5 m²/g. At the lower limit it is possible for the surface area to be as low as 0.2 m²/g. The BET method for determining surface area is described by R. B. Anderson in *Experimental Methods in Catalytic Research*, pp. 48-66, Academic Press, 1968. As noted hereinbefore, the silica matrix essentially does not contain a microporous or mesoporous structure; however, a large macroporous structure randomly permeates the matrix. The macropores range in diameter from 500 Å to about 4000 Å, as determined by mercury infusion techniques using, for example, a Micromeritics Model 9305 mercury porosimeter.

The composite comprising the silica matrix and the treated metal oxide may contain alkali metal ions derived from the alkali silicate solution. Accordingly, the composite will have basic properties. Should a less basic, neutral or acidic composite be desired, the composite may be ion-exchanged with an acid solution or an ammonium salt, such as ammonium nitrate, to the desired degree of acidity. In the case of the catalyst composition of this invention, the concentration of alkali metal ions may be reduced via ion-exchange to levels less than about 0.5 weight percent, preferably less than about 0.1 weight percent. The ion-exchange procedure is conducted after polymerization of the silicate (Step c) and prior to calcination (Step d). The molarity of the acid or ammonium salt solution is typically low, preferably ranging from about 0.1M to about 2M. The pH of the solution is typically in the range from about 7.5 to about 9.0, preferably in the range from about 8.2 to about 8.9. The ion-exchange procedure may be carried out simply by stirring the composite in a flask filled with the ion-exchange solution or by passing the solution through a column filled with composite. At least two ion-exchanges are preferred, and more may be beneficial.

Following the optional removal of alkali ions, the composite is dried for about 2 hr to about 10 hr at a temperature between about 60° C. and about 150° C. Thereafter, the composite is calcined at a temperature ranging from about 400° C. to about 800° C. for a period of about 1 hr to about 10 hr to remove the blocking agent and to convert the source of metal oxide to the metal oxide. After calcination a composite material is obtained comprising the above-described silica matrix having encapsulated therein discrete regions of metal oxide phase. Calcination does not significantly change the morphology or surface area of the silica matrix. For the specific case of magnesium oxide, the BET surface area of the magnesium oxide phase ranges from about 70 m²/g to about 170 m²/g. Accordingly, the calcined composite material has a BET surface area ranging from about 30 m²/g to about 150 m²/g.

The calcined composite comprising the silica matrix and metal oxide can be impregnated with any catalytic metal or metal compound to form a hard catalyst composition. For example, a composite comprising the silica matrix and magnesium oxide can be impregnated with a solution containing a source of molybdenum oxide to form a strong catalyst composition which is active in the process of this invention. The impregnation technique is described by Charles N. Satterfield in *Heterogeneous Catalysis in Practice*, McGraw-Hill Book Company, New York, 1980, pp. 82-83, which is incorporated herein by reference. Any source of molybdenum oxide is acceptable, including for example, $MoO_3$, $(NH_4)_2Mo_2O_7$, $(NH_4)_6Mo_7O_{24}\cdot 4H_2O$, and $(NH_4)_2MoO_4$. The molybdenum oxide can also be obtained from a precursor molybdenum compound, such as molybdenum carbonyls, e.g., $Mo(CO)_6$. Preferably, the molybdenum is in the +4 to +6 oxidation state. Preferably, the source of molybdenum oxide is ammonium heptamolybdate represented by the formula $(NH_4)_6Mo_7O_{24}\cdot 4H_2O$. Generally, the desired quantity of a molybdenum oxide or precursor compound is dissolved in a solvent, preferably water, to make a solution. The solution is brought into contact with the composite material and the resulting slurry is dried to remove solvent. If the solution is aqueous, the drying is conducted in an oven at a temperature in the range from about 70° C. to about 120° C. Thereafter, the dried slurry is calcined to form a catalytically active composition containing the silica matrix, magnesium oxide and molybdenum oxide. The calcination is typically conducted at a temperature ranging from about 300° C. to about 900° C. for a time ranging from 0.5 hour to about 24 hours. Preferably, the calcination is conducted at a temperature in the range from about 500° C. to about 800° C., more preferably, from about 550° C. to about 650° C. Alternatively, the dried slurry, described hereinabove, can be employed directly with no prior calcination in the catalytic process of this invention. Since the molybdenum precursor can be converted into molybdenum oxide at or about 300° C., and since the catalyst bed is heated to a temperature higher than about 300° C., the dried composition will be converted in situ into the catalytically active magnesium and molybdenum oxides. As noted hereinbefore, calcination essentially does not change the basic morphology of the composite. The molybdenum oxide is associated with the magnesium oxide particles and not with the silica matrix, as shown by TEM.

The elemental analysis of the calcined solid reveals a composition ranging from about 3 weight percent $MoO_3$ to about 30 weight percent $MoO_3$, from about 72 weight percent MgO to about 7 weight percent MgO, and from about 25 weight percent silica to about 90 weight percent silica. Preferably, the composition ranges from about 5 weight percent $MoO_3$ to about 25 weight percent $MoO_3$, from about 25 weight percent MgO to about 70 weight percent MgO, and from about 25 weight percent silica to about 70 weight percent silica. More preferably, the composition ranges from about 10 weight percent $MoO_3$ to about 20 weight percent $MoO_3$, from about 30 weight percent MgO to about 55 weight percent MgO, and from about 35 weight percent silica to about 50 weight percent silica.

It is beneficial to add a promoting amount of at least one alkali metal promoter to the catalyst component. The promoter serves to increase the selectivity to styrene or ethylbenzene or both and productivity of the process of this invention. Such a promoter is typically a compound of lithium, sodium, potassium, rubidium, cesium or francium of sufficient basicity to improve the selectivity in the process of this invention. Suitable compounds include the alkali oxides, hydroxides and carbonates. Compounds which decompose on heating to the oxides are also suitable, such as alkali metal acetates and oxalates. Alkali metal salts may be found which are also suitable, although typically, the alkali metal halides and alkali metal silicates are not preferred due to their lower basicity. Preferably, the alkali metal promoter is an alkali metal oxide, hydroxide, carbonate, acetate, or oxalate. More preferably, the alkali metal promoter is an oxide or hydroxide of potassium or cesium. Most preferably, the alkali metal promoter is an oxide or hydroxide of potassium.

The amount of alkali metal promoter significantly affects the selectivity of the third catalyst. Generally, any amount of alkali metal promoter is acceptable which is sufficient to increase the selectivity and the productivity of products in the process of this invention. Typically, the amount of alkali metal promoter calculated as the alkali hydroxide is in the range from about 0.01 weight percent to about 5 weight percent based on the combined weights of silica, magnesium oxide and molybdenum oxide. Preferably, the amount of alkali metal promoter calculated as the alkali metal hydroxide is in the range from about 0.02 weight percent to about 2 weight percent, more preferably, in the range from about 0.1 weight percent to about 1.0 weight percent, based on the combined weights of silica, magnesium oxide and molybdenum oxide. Below the lower preferred amount of alkali metal promoter the selectivity to styrene or ethylbenzene or both is reduced while the selectivity to deep oxidation products is increased. Above the upper preferred amount of alkali metal promoter the selectivity and productivity to styrene or ethylbenzene or both are also reduced.

The alkali metal promoter can be added to the catalyst component in a variety of ways known to those in the art. For example, the promoter can be applied by the impregnation technique, noted hereinbefore. In this technique the molybdenum-impregnated composite is immersed in a solution of the alkali metal promoter, for example, a methanolic solution of the alkali metal oxide or hydroxide. The alkali-impregnated composite is then drained of excess solution, dried in an oven to remove residual solvent, and calcined at a temperature in the range from about 550° C. to about 650° C. Alternatively, the alkali metal compound can be impregnated from the same solution as the molybdenum compound.

Optionally, the catalyst component of this invention can contain an activator which functions to increase the activity of the catalyst at any given temperature. Preferably, the activator does not decrease significantly the selectivity to aromatic products. Preferably, the activator allows the reaction to be run at a lower temperature, while achieving high selectivity and high productivity to styrene or ethylbenzene or both. Activators which are suitable for incorporation into the catalyst include the oxides of vanadium, preferably $V_2O_5$. Any amount of vanadium oxide can be added to the catalyst provided that (1) the activity of the catalyst is increased, and (2) the selectivity for styrne or ethylbenzene or both is not significantly decreased. Generally, if an activator is used, the concentration ranges from about 0.05 weight percent to about 10 weight percent based on the total weight of the catalyst composition. Preferably, the concentration of activator ranges from about 0.10 weight percent to about 5.0 weight percent, more preferably, from about 0.15 weight percent to about 2.0 weight percent. The activator can also be applied to the composite by the impregnation technique.

When desired, the catalysts of the present invention can be regenerated by techniques known to those skilled in the art. For example, the catalysts can be regenerated by passing an oxygen-containing gas over the catalyst at elevated temperatures.

The feedstream to be converted in accordance with this invention comprises butadiene. The butadiene need not be 100 percent pure and can contain other hydrocarbons such as alkanes, alkenes, cyclic aliphatics, and aromatics. Thus, this invention is useful for converting butadiene found in feedstreams of crackers, for example, which are utilized widely in industry. The feedstream can also comprise inert carrier gases such as nitrogen, helium, argon, carbon dioxide, and steam. The feedstream is substantially free of gaseous oxygen with no greater than about 1 percent by volume of the feedstream being gaseous oxygen. A feedstream useful in this invention contains greater than about 10 percent by volume of butadiene. Preferably, the feedstream contains greater than about 20 percent by volume of butadiene.

The process of the present invention is carried out in the gas phase at a temperature in the range from about 400° C. to about 625° C. Preferably, the temperature is from about 450° C. to about 600° C. The pressure can be subatmospheric, atmospheric, or superatmospheric. Preferably, the pressure is superatmospheric. When pressure is superatmospheric, it is preferred that the pressure be less than about 25 atmospheres, more preferably less than about 10 atmospheres.

The processes of the present invention can be carried out in the gas phase in a variety of flow reactors. Examples of suitable reactors include batch reactors, continuous fixed-bed reactors, fluidized bed reactors, and moving bed reactors. Preferably, the reactor is a continuous flow reactor such as a fixed-bed reactor or is a moving bed reactor such as a raining solids reactor or a riser reactor. The flow rate of feedstream in a continuous flow reactor is expressed as the gas hourly space velocity (GHSV) and is given in units of volume of gaseous feedstream per total reactor volume per hour or simply $hr^{-1}$. The reactor can be operated with a flow rate of reactant in the range from about 100 $hr^{-1}$ to about 36,000 $hr^{-1}$. A more preferred commercial reactor for the process of this invention is a moving bed reactor, such as a riser reactor. In moving bed reactors the catalyst particles are subjected to constant impact with other catalyst particles and with the walls of the reactor. Such forces gradually reduce the size of the catalyst particles to small fines which are lost in the reaction products; thus, the useful lifetime of the catalyst is greatly limited. Consequently, it is required for the catalyst to be prepared in a form which is able to withstand high impact and erosion forces. A preferred catalyst is the alkali-promoted magnesium molybdate catalyst supported on silica, alumina, or magnesium-alumina.

Typically, a riser reactor comprises an upright vessel of relatively low ratio of diameter to length. The catalyst is continuously charged into the bottom of the riser reactor. Likewise, the butadiene feedstream is delivered concurrently to the bottom of the riser reactor as a vapor phase feed or as a liquid phase feed. Preferably, the butadiene feedstream is delivered as a vapor phase feed. The butadiene feedstream moves upward through the reactor, thereby contacting the catalyst. The feedstream and catalyst rise through the reactor and the butadiene is transformed in a single pass to form products of the process. The catalyst is typically separated from the feedstream and products of the process by use of a stripping gas which is delivered to the reactor after the feedstream and catalyst have contacted to produce products. Any conventional stripping gas can be used for this purpose, but VCH is preferred. The product stream exits the riser reactor and is separated by known methods, such as distillation, condensation, adsorption, and zone freezing, to recover the desired products.

Unreacted butadiene can be recycled to the riser reactor for further conversion.

The operation of a riser reactor can be simulated by employing a method of alternating pulses of butadiene diluted by an inert gas through a fixed catalyst bed such that the volume ratio of butadiene to catalyst is high. Thus, a pulse of a butadiene feedstream is passed through the catalyst bed wherein the butadiene is converted to products. Next, a pulse of stripper gas is passed through the catalyst bed to purge the bed of residual hydrocarbons. When required, the catalyst can be regenerated by passing an oxygen-containing gas over the catalyst at elevated temperatures. Likewise, in a riser reactor, it is preferred to maintain a high ratio of gas volume to catalyst volume. In other words, a low catalyst loading should be employed in a riser reactor.

When the process of this invention is conducted in a moving bed reactor, described hereinbefore, the flow rate of the reactants can be varied. Generally, in the process of this invention the butadiene feedstream is fed into the reactor at any operable flow rate which promotes the formation of products and yields the desired conversion and selectivity. Preferably, the flow rate of the feedstream in the moving bed reactor is about 100 hr$^{-1}$ to about 20,000 hr$^{-1}$. It should be understood that the space velocity controls the residence time of the reactants. Residence times suitable in the practice of this invention are from about one-half second to 10 seconds, preferably from about 1 to 10 seconds. Desirable residence times are inversely related to pressure. Thus, as pressure in the reactor is increased, the more preferable residence time is lowered. The most desirable residence times are readily determined by a skilled artisan depending on the pressure in the reactor as well as other process conditions.

For the purposes of this invention, "conversion" is defined as the mole percentage of butadiene lost from the feedstream as a result of reaction. The conversion can vary widely depending upon the reactants, the form of the catalyst, and the process conditions such as temperature, pressure, flow rate, and catalyst residence time. Within the preferred temperature range, as the temperature increases the conversion generally increases. Within the preferred gas hourly space velocity range, as the space velocity increases the conversion generally decreases. Typically, the conversion of butadiene is at least about 10 mole percent. Preferably, the conversion is at least about 20 mole percent; more preferably, at least about 30 mole percent; even more preferably, at least about 40 mole percent; and most preferably, at least about 50 mole percent.

For the purposes of this invention, "selectivity" is defined as the mole percentage of converted butadiene which forms ethylbenzene or styrene or both. Generally, selectivities also vary widely depending upon the reactants, the form of the catalyst, and the process conditions. Typically, the process of this invention achieves high selectivities to ethylbenzene and styrene. Within the preferred temperature range, as the temperature increases the selectivity generally decreases. Within the preferred space velocity range, as the space velocity increases the selectivity generally increases. Typically, the selectivity to ethylbenzene and styrene is greater than about 40 mole percent. Preferably, the selectivity to ethylbenzene and styrene is greater than about 50 mole percent, more preferably greater than about 60 mole percent, most preferably greater than about 70 mole percent.

The concept of simultaneous high conversion and high selectivity can be conveniently expressed in terms of yield. For the purposes of this invention, the term "yield" refers to the numerical product of the single-pass conversion and selectivity. For example, a process according to the present invention operating at a conversion of 0.65, or 65 mole percent, and a selectivity of 0.75, or 75 mole percent, would have a yield of 0.49, or 49 mole percent. Typically, the yield achieved in the process of this invention is at least about 8 mole percent. Preferably, the yield achieved in the process of this invention is at least about 18 mole percent, more preferably at least about 28 mole percent, most preferably at least about 35 mole percent.

Subsequent to aromatization of at least a portion of the butadiene feedstream, the products can be separated and recovered by conventional techniques. For example, the product can be condensed to form a liquid and residual butadiene can be removed by vacuum or distillation. Recovered butadiene can be recycled to the reactor, thus facilitating very high conversions of unsaturated hydrocarbons of up to 100 percent.

The following examples are given to illustrate the invention and should not be construed as limiting its scope. All parts and percentages are by weight unless otherwise indicated.

EXAMPLE 1

Conversion of Butadiene to Styrene over a Molybdenum-Magnesium Catalyst

A ½-inch cylindrical quartz reactor is filled with 27 cm of quartz chips. One gram of a catalyst consisting essentially of 22 weight percent $MoO_3$ and 0.3 weight percent potassium on a MgO support with a surface area of about 115 square meters per gram is interspersed in the void volume. The oxide of molybdenum in the catalyst has an oxidation state less than or equal to $+6$ and greater than $+4$. The reactor assembly is placed in a heater for temperature control. The reaction is carried out in a pulsed mode. A switching valve diverting flowing reactant into the reactor for short time intervals of a minute or less. The products of the reaction is measured with an on-line gas chromatograph through a small volume (heat traced) sampling line. Samples are analyzed early in the reaction pulse in order to obtain initial products from the several second residence time in the reactor volume. When the feed composition is 45 percent butadiene in nitrogen and a GHSV of 220 hr$^{-1}$, a conversion of 22 percent is observed at 560° C. and 1.7 psig. The selectivity to styrene is 74 percent. Other useful products in descending abundance are VCH (12.5 mole percent), ethylbenzene (5.5 mole percent), benzene (4.3 mole percent), and toluene (2.0 mole percent) with a combined selectivity of 24 percent. The overall selectivity to styrene, VCH, ethylbenzene, benzene, and toluene is 98 percent to these products. The styrene to ethylbenzene ratio is greater than ten.

EXAMPLE 2

Conversion of Butadiene to Styrene over a Molybdenum-Magnesium Catalyst

The procedure of Example 1 is repeated except the feed composition is 12 percent butadiene in nitrogen. The conversion is reduced to seven percent, but the selectivity to styrene increases slightly to 83 percent.

What is claimed is:

1. A process for the production of aromatic compounds from butadiene which comprises contacting a feedstream comprising butadiene with a catalyst at a temperature in a range of from 400° C. to about 625° C. and a flow rate of the feedstream in the range from about 100 hr$^{-1}$ to about 36,000 hr$^{-1}$ and under conditions effective to convert at least a portion of the butadiene to ethylbenzene or styrene or both, wherein the catalyst is an oxide of molybdenum and a Group IA alkali metal promoter on a support selected from the group consisting of silica, alumina, or a magnesium-alumina composite, or an oxide of molybdenum and a Group IA alkali metal promoter on a magnesium oxide support, and wherein the oxide of molybdenum in the catalyst has an oxidation state less than or equal to +6 and greater than +4.

2. The process of claim 1 wherein the catalyst consists essentially of an oxide of magnesium, an oxide of molybdenum, and a Group IA alkali metal promoter in a concentration from about 0.1 weight percent to about 5 weight percent calculated as the alkali hydroxide and based on the combined weight of the magnesium and molybdenum oxides, and optionally containing an oxide of vanadium.

3. The process of claim 1 wherein the process is run continuously.

4. The process of claim 1 wherein the process is conducted under conditions such that the selectivity to styrene and ethylbenzene is greater than about 40 mole percent.

5. The process of claim 1 wherein the process is run in a moving bed reactor wherein the flow rate of the feedstream is from about 100 hr$^{-1}$ to about 20,000 hr$^{-1}$.

6. The process of claim 1 wherein the catalyst is an oxide of molybdenum and a Group IA alkali metal promoter on a support of silica.

7. The process of claim 1 wherein the pressure is superatmospheric.

8. The process of claim 7 wherein the pressure is less than about 10 atmospheres.

9. The process of claim 1 wherein residence time of the butadiene is from about 1 second to about 10 seconds.

* * * * *